United States Patent [19]

Webster

[11] Patent Number: 4,738,535
[45] Date of Patent: Apr. 19, 1988

[54] OPTICAL INSTRUMENT EMPLOYING FIBER OPTICS TO DIRECT LIGHT THROUGH TILTING FILTER WHEEL

[75] Inventor: Donald R. Webster, Laurel, Md.

[73] Assignee: Pacific Scientific Company, Anaheim, Calif.

[21] Appl. No.: 888,122

[22] Filed: Jul. 22, 1986

[51] Int. Cl.⁴ .............................................. G01J 3/51
[52] U.S. Cl. .................................... 356/418; 250/227
[58] Field of Search ............... 250/226, 227; 356/409, 356/414, 418; 356/326

[56] References Cited

U.S. PATENT DOCUMENTS

| | | | |
|---|---|---|---|
| 3,596,083 | 7/1971 | Lovering | 240/41 |
| 3,622,793 | 11/1971 | Dalton | 250/227 X |
| 3,709,612 | 1/1973 | Clemens . | |
| 3,861,788 | 1/1975 | Webster | 350/315 |
| 3,885,879 | 5/1975 | Louder et al. | 356/326 |
| 4,084,909 | 4/1978 | Mathisen | 356/418 |

FOREIGN PATENT DOCUMENTS 2155173 9/1985 United Kingdom ................ 356/326

Primary Examiner—Vincent P. McGraw
Attorney, Agent, or Firm—Lane and Aitken

[57] ABSTRACT

In an optical instrument, fiber optics are employed to receive light from a linear filament. The fiber optics are arranged into a plurality of light receiving bundle ends distributed around the linear filament and shaped into narrow rectangular slits aligned with the filament. The fibers from each of the receiving ends are equally distributed between two transmitting ends which direct the light through cylindrical lenses to opposite sides of a rotating filter wheel in a paddle wheel configuration. Light beams from the transmitting ends of the fiber optic bundles pass through filters on the filter wheel to additional fiber optic bundles which carry the received light to a probe.

11 Claims, 2 Drawing Sheets

OPTICAL INSTRUMENT EMPLOYING FIBER OPTICS TO DIRECT LIGHT THROUGH TILTING FILTER WHEEL

BACKGROUND OF THE INVENTION

This invention relates to an optical instrument and more particularly to an optical instrument employing tilting filters to scan the wavelength of light transmitted to a measurement subject through a spectral range.

In U.S. Pat. Nos. 3,861,788 to Donald A Webster and 4,082,464 to Robert A. Johnson, there are disclosed optical instruments designed to measure reflectivity or transmissivity of a measurement subject by directing light with a very narrow wavelength band onto the measurement subject and measuring the resulting light emanating from the measurement subject such as by reflection by or transmission through the measurement subject. In the instruments, a plurality of interference filters are mounted on a filter wheel and each filter is rotated by the filter wheel sequentially into the path of collimated light in the near infrared range. As the filter moves through the beam of collimated light, the angle of the filter to the instrument light varies and the narrow bandwidth of light transmitted by the filter is changed. In this manner the center wavelength of th narrow wavelength band transmitted to subject is swept through a selected spectrum, specifically, the near infrared spectrum.

SUMMARY OF THE INVENTION

The present invention is an improvement on the above described optical instruments. In accordance with the invention, fiber optics are employed to enable the instrument to be reduced substantially in size and thus, made compact and portable. Also, the fiber optics facilitate the transmission of the light to a wide variety of types of measurement subjects. In the specific embodiment of the invention, the light is transmitted to a human subject to measure the oxygen content in the blood through the skin of the subject.

In accordance with the invention, a source of light preferably, near infrared light, is provided having a linear filament. Optic fibers are arranged into a plurality of light receiving bundle ends distributed around the light source. The entrance ends of the fiber optic bundle are shaped into narrow rectangular slits, which are aligned with the filament of the lamp. As a result, the light entering each fiber optic bundle entrance ends will converge along only one axis. The fibers from each of the fiber optic bundle entrance ends are distributed into two fiber optic bundle transmitting ends, which direct the light to opposite sides of a rotating filter wheel in a paddle wheel configuration. Light beams from the transmitting ends of the fiber optic bundles pass on opposite sides of the axis of the tilting filter wheel through filters on the filter wheel and are received by fiber optic bundles, which carry the received light to a probe for directing the light onto the measurement subject. Additional fiber optic bundles are provided in the probe to receive the resulting light emanating from the measurement subject and carry the light to photodetectors.

Each of the two transmitting bundle ends which transmit light to the opposite sides of the filter wheel has optic fibers coming from all of the receiving bundle ends equally distributed so that if the light source is not precisely centered among the receiving ends causing a different intensity of light to be received by different bundles, the transmitting ends will still transmit the same average intensity. The transmitting bundle ends are shaped into narrow slits to reduce the bandwidth of the light transmitted through the filters. Because the light received in the optic fibers the light source converges along only one axis, the light emitted from the transmitting ends to the opposite sides of the tilting filter wheel will for the most part diverge along one axis. Cylindrical lenses are provided between the transmitting ends and the tilting filter wheel to collimate the light emitted from the transmitting ends. The fact that most of the light rays emitted from the transmitting ends of the optic fiber are diverges along only one axis means that a high degree of collimation can be achieved with a cylindrical lens. Lenses are provided on the opposite side of the filter wheel from the collimating lenses to focus the light transmitted through the filter wheel onto the receiving ends of the fiber optic bundles leading to the measurement probe.

DESCRIPTION OF A PREFERRED EMBODIMENT

Figure 1:
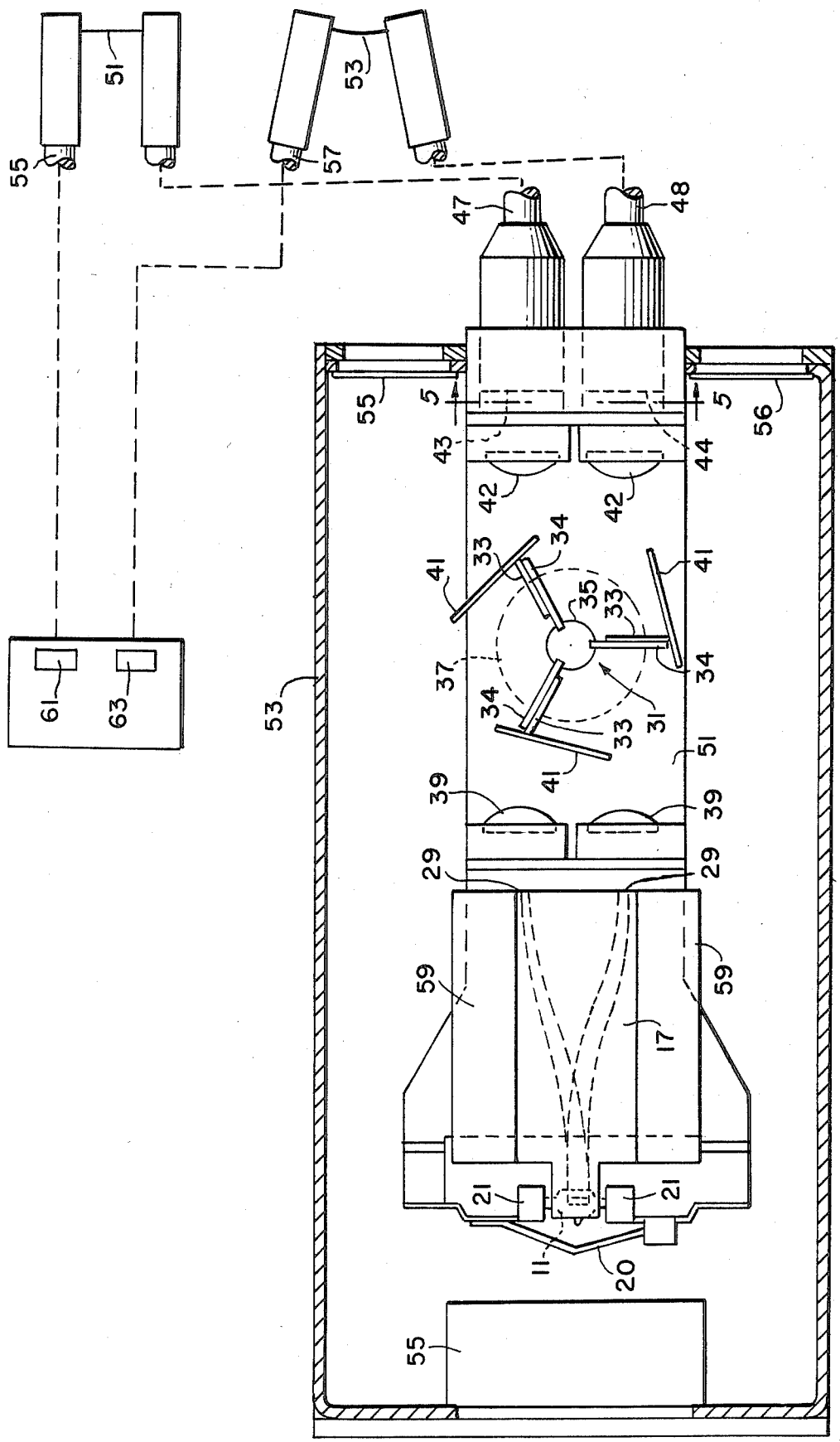
FIG. 1 is a partial sectional view in elevation of the instrument of the invention.

As shown in the drawings, the optical instrument of the invention comprises a lamp 11 having a linear filament 13. The lamp is disposed in a recess 15 defined in a central end projection 19 of a fiber optic mounting block 17. The recess 15 extends through the end projection 19 from the top wall thereof to the bottom wall thereof. The lamp 11 is mounted in a fixture 20 having sockets 21 positioned above and below the end projection 19 and the lamp 11 is connected between the sockets 21. The recess 15 has four vertical walls 23 each making a 120 degree angle with the adjacent vertical wall. A bundle of optic fibers 16 is mounted in the block 17 extending from the walls 23 to the transmitting end 25 of the fiber optic mounting block 17. At the walls 23, the bundle of optic fibers is divided into four receiving bundle ends 27 with each bundle end 27 facing the filament 13 of the lamp 11. The bundle ends 27 are shaped into rectangular slits, which are 2.4 millimeters wide and 6 millameters long. With this arrangement each optic fiber in the bundle 16 has a receiving end pointed perpendicularly at the linear filament 13 of the lamp 11. As a result, the light entering each optic fiber from the lamp will be substantially collimated with respect to the horizontal dimension. At the transmitting end 25 of the fiber optics mounting block 17, the bundle of optic fibers is divided into two transmitting ends 29. The transmitting ends 29 are arranged into narrow rectangular slits 1.5 mm by 20 mm, one above each other in the transmitting end 25 of the fiber optic mounting block. The optic fibers from each receiving bundle end 27 are equally distributed between the two transmitting bundle ends 29. The fiber optic bundle ends 29 are pointed towards opposite sides of the axis of a tilting filter wheel 31, which comprises three interference filters 33 mounted on an axle 35 in a paddle wheel configuration. The axle 35 is driven by a motor 37 to rotate the interference filters on the axle 35.

Because the light received by receiving ends of the optic fibers is substantially collimated with respect to horizontal, the light emitted from the transmitting ends of the optic fibers at bundle ends 29 will be substantially collimated with respect to horizontal because most of the fibers will retain the same orientation at the transmitting ends. The light will spread vertically from the transmitting ends because each fiber will receive light spread through a vertical angle from the linear filament. The light beams pass through cylindrical lenses 39 which collimate vertical spread in the rays emitted from the transmitting fiber optic bundle ends 29. As a result, beams of collimated light are formed to pass on opposite sides of the axle 35. Because of the shape of the transmitting ends 29 into narrow slits, the light will beams will be in the form of narrow sheets of light with the planes of the beams parallel to the axis of the axle 35, but with the direction that the light is transmitted perpendicular to a plane containing the axis of the axle 35. Because the optic fibers from each receiving bundle end 27 of the fiber optics mounted in the mounting block 17 are equally distributed between the transmitting bundle ends 29, the light beams emitted from the transmitting bundle ends 29 will have the same intensity even if the lamp 11 is not positioned precisely centered in the recess 15.

As the motor 37 rotates the filter wheel 31, the filters 33 will be moved in sequence through each of the two beams of light. As each of the filters 33 moves through a beam of light, the angle of incidence of the beam on the filter will vary. As a result, the narrow bandwidth of light transmitted by the interference filter as it is rotated through one of the beams of light will be swept through a portion of the near infrared range. The three filters 33 are selected to cover different portions of the near infrared range which overlap so that the entire desired portion of the near infrared spectrum is covered.

Figure 2:
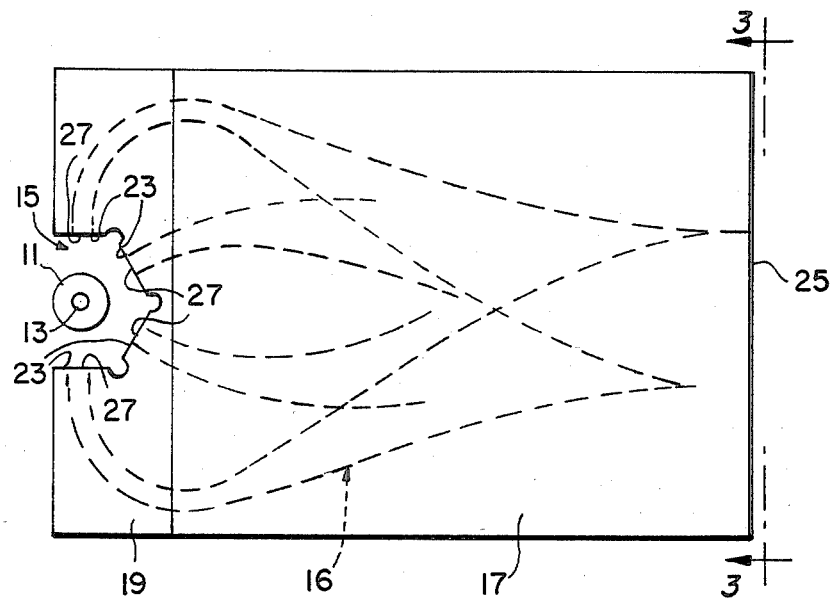
FIG. 2 is a top plan view of the fiber optic mounting block and lamp employed in the instrument of FIG. 1.
Figure 3:
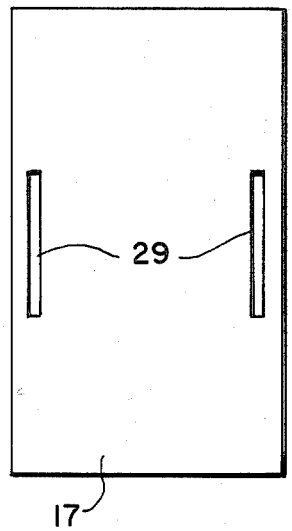
FIG. 3 is an end view of the fiber optic mounting block taken along line 3—3 of FIG. 2.
Figure 4:
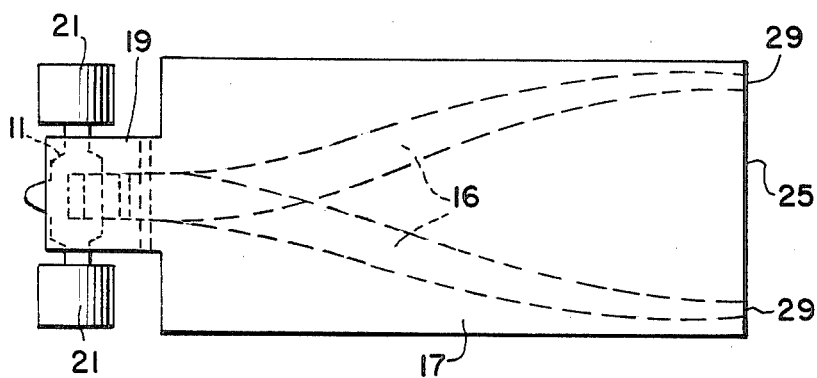
FIG. 4 is a side view in elevation of the fiber optic mounting block and lamp.
Figure 5:
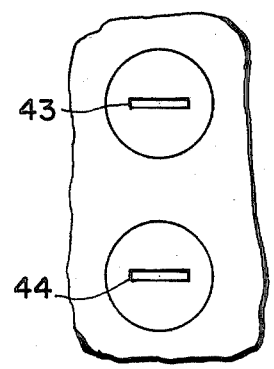
FIG. 5 is an end view taken along line 5—5 in FIG. 1 to illustrate the ends of fiber optic bundles for transmitting light to the probe of the instrument of the present invention.

The filters 33 are mounted in arms 34 which extend from the axle 35. Mounted on the ends of the arms 34 are opaque vanes 41. These vanes serve to block the beams of light between times adjacent filters are being moved through the beams of light to provide dark periods for zeroing of the instrument as explained in U.S. Pat. No. 3,861,788. For example, if a filter wheel is rotated clockwise as shown in FIG. 2, then as each filter 33 is moved into the upper beam of light as shown in FIG. 1, the vane mounted on the end of the arm for this filter will block the light until the filter 33 becomes almost perpendicular to the light beam. Then as the filter continues to rotate, the light will be transmitted through the filter and the center wavelength of the transmitted band will be varied. The vanes will block the light in a similar manner for the lower beam of light except that the light is blocked on the upstream side of the filter wheel for the upper light beam and on the downstream side of the light beam for the lower light beam.

The light beams upon passing through the filters of the filter wheels will tend to spread a small amount. Lenses 42 are provided to refocus the light beams into narrow slits of light onto the receiving ends 43 and 44 of fiber optic bundles 47 and 48. The receiving ends 43 and 44 are shaped into narrow slits to correspond to the shape of the light beam focused onto the receiving ends 43 and 44.

As shown in FIG. 1, the fixture 20, the fiber optic mounting block 17, the lenses 19, the lenses 42, and the ends 43 and 44 of the bundles 47 and 48 are mounted on a chassis 51 enclosed within a housing 53. A fan 55 is provided to exhaust air from the rear of the housing 53 and draw air into the housing through filter screens 55 and 56 mounted in the front wall of the housing. Heat sinks 59 having vertically extending parallel fins are mounted on the top and bottom surface of the fiber optic mounting block 17 to be cooled by the air flow generated by the fan 55.

The fiber optic bundle 47 carries the light received through the filter wheel 31 to a probe 51 adapted to be applied to the torso of the human body. The fiber optic bundle 48 carries the light transmitted through the tilting filter wheel to a probe 53 adapted to be applied to the forehead of the human body. The receiving end of a fiber optic bundle 55 is mounted in the probe 51 spaced 40mm from the fiber optic bundle 47. When the probe 51 is placed on the torso of the human body and light is transmitted through the bundle 47, the resulting irradiation through the skin of the torso will cause reflections back to the fiber optic bundle 55, which will carry the reflected light to a photodetector 61. The probe 53 has the receiving end of a fiber optic bundle 57 mounted therein adapted to be positioned at an angle to the transmitting end of the fiber optic bundle 48 and separated therefrom by about 40 mm. When the probe 53 is applied to the forehead of a subject and light from the tilting filter wheel is transmitted through the bundle 48 and irradiates the blood vessels of the subject through the forehead, light will be reflected back through the skin to the bundle 57 which will carry the light to a photodetector 63. By means of the signals generated by the photodetectors 61 and 63, the instrument can be employed to measure the degree of oxygen in the blood of the subject.

In the instrument as described above, the fiber optic arrangement used to transmit light between the lamp and the rotating filters improves collimation of the light transmitted through the filters and thus, reduces the band width of the transmitted light. In addition, the fiber optic arrangement permits the instrument to be organized into a compact form facilitating its portability. The distribution of the fibers between the bundle ends receiving the light from the lamp and the bundle ends transmitting the light to the filter wheel so that the two light beams transmitted on each side of the filter wheel have the same intensity, makes possible reliable comparison of the measurement by each probe.

Instead of having the receiving ends of the optic fiber facing the lamp filament formed into separate linear bundles, they could be distributed around the filament in a continuous cylinder to achieve the desired collimation. The important feature is that the receiving end of each optic fiber is pointed at the linear filament. The linear bundles are used to facilitate fabrication of the instrument.

The specific embodiment of the invention as described above is designed for measuring oxygen content in the blood of a human subject. The concept of employing fiber optics in combination with the tilting filter wheel and a fiber optic probe to provide a compact optical instrument can be used in a wide variety of applications of analysis. Instead of employing reflected light, the instrument probe could be designed to measure light transmitted through samples. Also, instead of using infrared light, the instrument could be designed to operate in the visible spectrum, for measuring color for example. These and other modifications may be made to the above described specific embodiment of the invention without departing from the spirit and scope of the invention, which is defined in the appended claims.

What is claimed is:

1. An optical instrument comprising a lamp having a linear filament distributed along an axis, fiber optics to receive light from said lamp and form the light received from said lamp into a beam, said fiber optics comprising a plurality of optic fibers having receiving ends distributed at different angles around said axis and arranged to receive light from said lamp simultaneously, each fiber being pointed perpendicularly at said filament, and means to rotate a filter through said beam to vary the wavelength transmitted through said filter.

2. An optical instrument as recited in claim 1, wherein the receiving ends of said fiber optics are arranged into a plurality of receiving bundle ends shaped into narrow slits facing said filament and aligned with said filament.

3. An opitcal instrument as recited in claim 2, wherein said optic fibers are arranged into two transmitting ends to form the light received by said fiber optics into two parallel beams, said optic fibers from each of said receiving bundle ends being equally distributed between said transmitting ends, said means to rotate a filter comprises a filter wheel having a plurality of filters and axle and means to rotate said filters on said axle to move said filters in sequence through said beams.

4. An optical instrument as recited in claim 3, wherein said filters vary the bandwidth of the transmitted light in accordance with the angle of the incidence of the light upon said filters, said instrument further comprising means for forming said beams into the shape of sheets of light in parallel to the axis of said filter wheel.

5. An optical instrument as recited in claim 1, wherein said filter varies the bandwidth of the transmitted light in accordance with the angle of incidence of the light upon said filter, said optic fibers being formed into at least one transmitting bundle end to form the light received by said fiber optics into said beam, and a cylindrical lens is positioned between said end and said filter to collimate the light emitted from said transmitting end.

6. An optical instrument as recited in claim 5, wherein said transmitting end is formed into a narrow slit and said cylindrical lens forms the beam of light emitted by said transmitting end into the form of a sheet.

7. An optical instrument comprising a lamp, fiber optics arranged to receive light from said lamp and form the light received thereby into two parellel beams, a filter wheel having a plurality of filters mounted thereon in a paddle wheel configuration and having an axle positioned between said beams with the beams passing through filters on said filter wheel on the opposite sides of said axle, and means to rotate said filter wheel on said axle to move said filters in sequence through said beams.

8. An optical instrument as recited in claim 7, wherein said fiber optics comprises a plurality of optic fibers haivg receiving ends arranged into bundles and distributed around said lamp with each bundle facing said lamp, said bundles being arranged to receive light simultaneously from said lamp, the optic fibers from each of said bundles being equally distributed into two transmitting ends, which form the light received by said fiber optics into said beams.

9. An optical instrument as recited in claim 8, wherein said lamp has a linear filament and wherein said bundles of receiving ends are distributed at different angles around the axis of said filament, said bundle ends being formed into slits aligned with said filament.

10. An optical instrument as recited in claim 7, wherein said filters vary the bandwidth of the transmitted light in accordance with the angle of incidence of the light upon such filter, means for forming said beams into the shape of sheets of light in planes parallel to the axis of said filter wheel.

11. An optical instrument as recited in claim 7, wherein a first fiber optic bundle is positioned to receive one of said beams of light after it passes through a filter on said filter wheel and a second fiber optic bundle is positioned to receive the other one of said beams of light after it passes through a filter on said filter wheel.

* * * * *